US012576286B2

(12) United States Patent
Kuroki

(10) Patent No.: US 12,576,286 B2
(45) Date of Patent: Mar. 17, 2026

(54) PARTICLE BEAM TREATMENT APPARATUS

(71) Applicant: SUMITOMO HEAVY INDUSTRIES, LTD., Tokyo (JP)

(72) Inventor: Toshiki Kuroki, Ehime (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 426 days.

(21) Appl. No.: 18/100,903

(22) Filed: Jan. 24, 2023

(65) Prior Publication Data

US 2023/0241418 A1 Aug. 3, 2023

(30) Foreign Application Priority Data

Jan. 28, 2022 (JP) ................................. 2022-011819

(51) Int. Cl.
*A61N 5/10* (2006.01)

(52) U.S. Cl.
CPC .... *A61N 5/1081* (2013.01); *A61N 2005/1094* (2013.01)

(58) Field of Classification Search
CPC .... A61N 2005/1094; A61N 2005/1061; A61N 2005/1087; A61N 5/1043; A61N 5/10
See application file for complete search history.

(56) References Cited

U.S. PATENT DOCUMENTS

| | | | | | |
|---|---|---|---|---|---|
| 5,986,274 A | * | 11/1999 | Akiyama | ................. | A61N 5/10 |
| | | | | | 250/492.1 |
| 5,993,373 A | * | 11/1999 | Nonaka | ................ | A61N 5/1081 |
| | | | | | 378/68 |

| | | | | | |
|---|---|---|---|---|---|
| 8,223,920 B2 | * | 7/2012 | Amelia | ................ | A61N 5/1049 |
| | | | | | 378/65 |
| 8,975,602 B2 | * | 3/2015 | Huber | .................. | A61N 5/1081 |
| | | | | | 250/492.1 |
| 10,179,251 B2 | * | 1/2019 | Kobayashi | ........... | A61N 5/1081 |
| 10,426,977 B2 | * | 10/2019 | Stacey | ................. | A61N 5/1049 |
| 10,695,587 B2 | * | 6/2020 | Yamashita | ........... | A61N 5/1081 |
| 10,835,766 B2 | * | 11/2020 | Kinugasa | ............. | A61N 5/1081 |
| 11,491,349 B2 | * | 11/2022 | Marash | ................ | A61N 5/1049 |

(Continued)

FOREIGN PATENT DOCUMENTS

| | | |
|---|---|---|
| JP | 2011-156263 A | 8/2011 |
| JP | 2017-012374 A | 1/2017 |
| JP | 2019-201730 A | 11/2019 |

*Primary Examiner* — Wyatt A Stoffa

(74) *Attorney, Agent, or Firm* — Michael Best & Friedrich LLP

(57) ABSTRACT

A particle beam treatment apparatus includes an irradiator that has an irradiation nozzle which irradiates an irradiation target with a particle beam and that is capable of moving rotationally in a vicinity of the irradiation target, a moving floor that extends on an annular trajectory surrounding the irradiation target along a rotation circumferential direction of the irradiator and that is movable on the annular trajectory depending on a position of the irradiator, a movable cover that is supported pivotably with respect to the irradiator or the moving floor and that covers a gap between the irradiator and the moving floor, and an adjusting mechanism that adjusts a pivoting position of the movable cover depending on the position of the irradiator such that a gap between the movable cover and the moving floor is covered.

16 Claims, 10 Drawing Sheets

(56)  References Cited

U.S. PATENT DOCUMENTS

| | | | |
|---|---|---|---|
| 2009/0304153 A1* | 12/2009 | Amelia | A61N 5/1081 |
| | | | 378/65 |
| 2011/0299657 A1* | 12/2011 | Havelange | A61N 5/1081 |
| | | | 378/65 |
| 2018/0064958 A1* | 3/2018 | Kobayashi | A61N 5/1081 |
| 2018/0289981 A1* | 10/2018 | Nagamoto | A61B 6/0442 |
| 2019/0001157 A1* | 1/2019 | Stacey | A61N 5/1081 |
| 2022/0184422 A1* | 6/2022 | Stahl | A61N 5/1067 |

* cited by examiner

PARTICLE BEAM TREATMENT APPARATUS

RELATED APPLICATIONS

The content of Japanese Patent Application No. 2022-011819, on the basis of which priority benefits are claimed in an accompanying application data sheet, is in its entirety incorporated herein by reference.

BACKGROUND

Technical Field

A certain embodiment of the present invention relates to a particle beam treatment apparatus.

Description of Related Art

Conventionally, a particle beam treatment apparatus of the related art is known. The particle beam treatment apparatus includes a gantry that is equipped with an irradiator which irradiates with a particle beam and that rotates in the vicinity of a treatment table and a moving floor that is disposed on an inner side of the gantry, that partitions a treatment room, and that moves around an annular trajectory in the vicinity of the treatment table. The annular trajectory of the moving floor is configured by a curved portion along a rotation circumferential direction of the gantry and a horizontal portion along a floor of the treatment room. Since the moving floor moves on a non-circular annular trajectory as described above while the irradiator rotates on a circular trajectory, a gap that is generated between the moving floor and the irradiator changes depending on the rotation position of the irradiator.

In order to cover the gap that is generated between the moving floor and the irradiator as described above, the moving floor is slidably connected to a side surface of the irradiator in the particle beam treatment apparatus of the related art. In this mechanism, instead of covering a gap in the side surface of the irradiator, a gap in the moving floor is generated at another place on the annular trajectory. Since the width of the gap changes depending on the rotation position of the irradiator, the gap is covered with a winding-type cover having a variable width. Also in the particle beam treatment apparatus of the related art below, the winding-type cover is adopted in order to cover the gap between the moving floor and the irradiator or the like.

SUMMARY

However, since it is necessary for such a winding-type cover to be a relatively soft member that can be wound, the winding-type cover is not limited to being capable of sufficiently supporting the weight of a person. Then, in a case where the gap is in the horizontal portion on the annular trajectory of the moving floor, it cannot be said that the person can walk safely on the moving floor even when the gap is covered with the winding-type cover. Therefore, in the particle beam treatment apparatus of the related art, it cannot be said that the gap in the moving floor is in a covered state in which safety can be ensured. In consideration of the problems, it is desirable to provide a particle beam treatment apparatus that allows covering a gap between an irradiator and a moving floor such that safety can be ensured.

According to an embodiment of the present invention, there is provided a particle beam treatment apparatus including an irradiator that has an irradiation nozzle which irradiates an irradiation target with a particle beam and that is capable of moving rotationally in a vicinity of the irradiation target, a moving floor that extends on an annular trajectory surrounding the irradiation target along a rotation circumferential direction of the irradiator and that is movable on the annular trajectory depending on a position of the irradiator, a movable cover that is supported pivotably with respect to the irradiator or the moving floor and that covers a gap between the irradiator and the moving floor, and an adjusting mechanism that adjusts a pivoting position of the movable cover depending on the position of the irradiator such that a gap between the movable cover and the moving floor is covered.

The movable cover may be supported pivotably with respect to the irradiator. The adjusting mechanism may include a first support portion that is provided at the irradiator and that supports one part of the movable cover and a second support portion that is provided at the moving floor and that supports the other part of the movable cover. The second support portion may allow displacement of the movable cover in a linear direction connecting the second support portion and the first support portion to each other.

The adjusting mechanism may include a guide rail that is provided at the movable cover and that extends on a line connecting the first support portion and the second support portion to each other, and the second support portion may include a roller that rolls on the guide rail. The movable cover may be supported pivotably with respect to the irradiator and may be capable of protruding to an outer region of the annular trajectory across the annular trajectory. The moving floor may include a plurality of floor members arrayed on the annular trajectory in a moving direction of the moving floor and may be bendable between the floor members.

DETAILED DESCRIPTION

Figure 1:
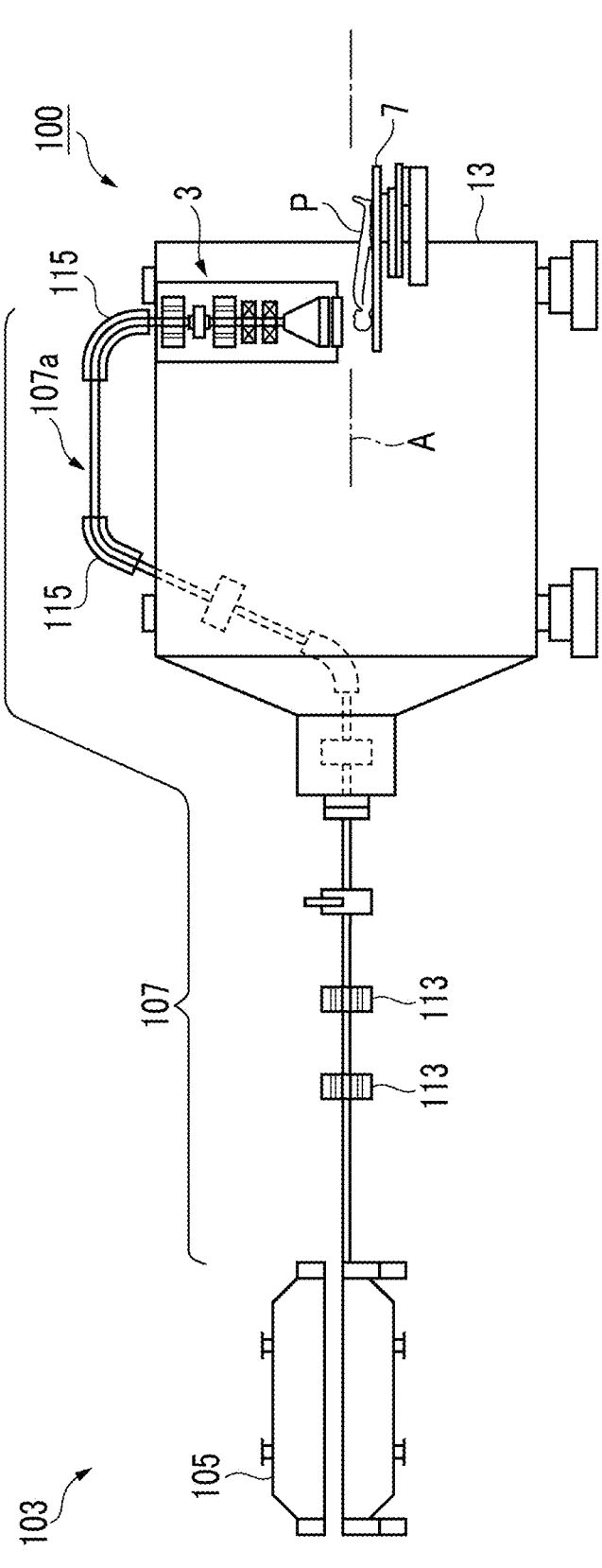
FIG. 1 is a view showing a charged particle beam treatment system into which a charged particle beam irradiation apparatus according to the present embodiment is incorporated.

Hereinafter, a particle beam treatment apparatus according to an embodiment of the present invention will be described in detail with reference to the drawings. In each drawing, each feature is exaggerated and depicted in some cases, the dimensional ratio and shape of each part of the particle beam treatment apparatus in the drawings do not necessarily match the actual ones, and the drawings do not necessarily match each other. As shown in FIG. 1, a charged particle beam irradiation apparatus 100 (particle beam treatment apparatus) of the present embodiment is incorporated into a charged particle beam treatment system 103 (for example, a proton beam treatment system). The charged particle beam irradiation apparatus 100 is an apparatus that performs treatment by irradiating a lesion (for example, a tumor or the like) inside a patient P (irradiation target) with a charged particle beam. Herein, the charged particle beam is, for example, a proton beam, a heavy particle beam, or the like.

The charged particle beam treatment system 103 includes an accelerator 105 that accelerates charged particles and emits charged particle beams, an irradiator 3 that irradiates the patient P with charged particle beams, a rotating gantry 13 that rotates the irradiator 3 about a horizontal rotation axis A in the vicinity of a treatment table 7 on which the patient P lies, and a transportation line 107 that connects the accelerator 105 and the irradiator 3 to each other and that transports charged particle beams from the accelerator 105 to the irradiator 3. Among these, the charged particle beam irradiation apparatus 100 includes a part of the transportation line 107, the rotating gantry 13, and the irradiator 3. The transportation line 107 includes a plurality of quadrupole electromagnets 113 for converging charged particle beams and a plurality of bending magnets 115 that bend the charged particle beams. Further, the transportation line 107 includes a plurality of ESSs (not shown) that selectively allow a charged particle beam having a desired energy width to pass, among transmitted charged particle beams.

Figure 2:
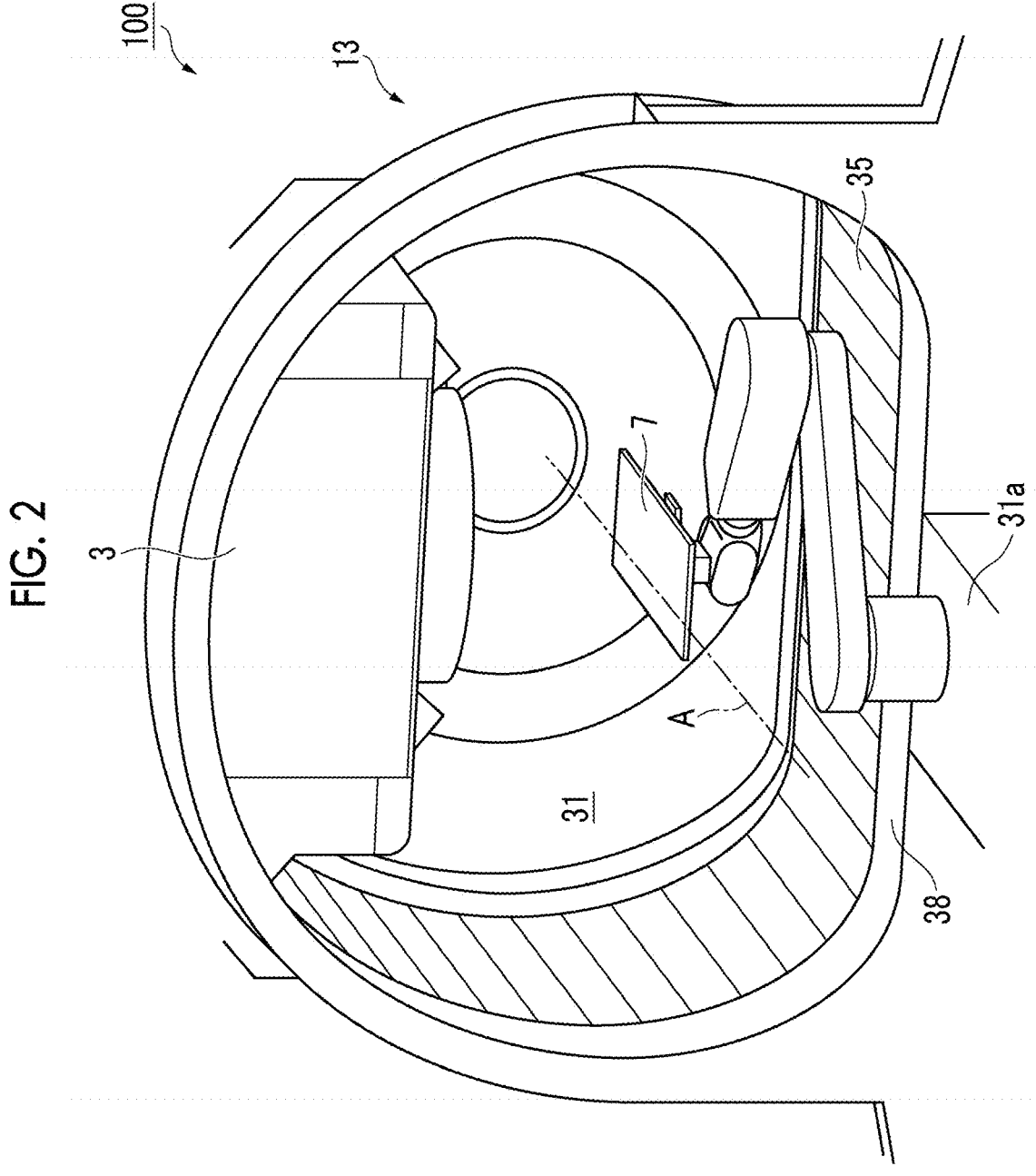
FIG. 2 is a perspective view showing a state where the charged particle beam irradiation apparatus is viewed from a treatment room side.
Figure 3:
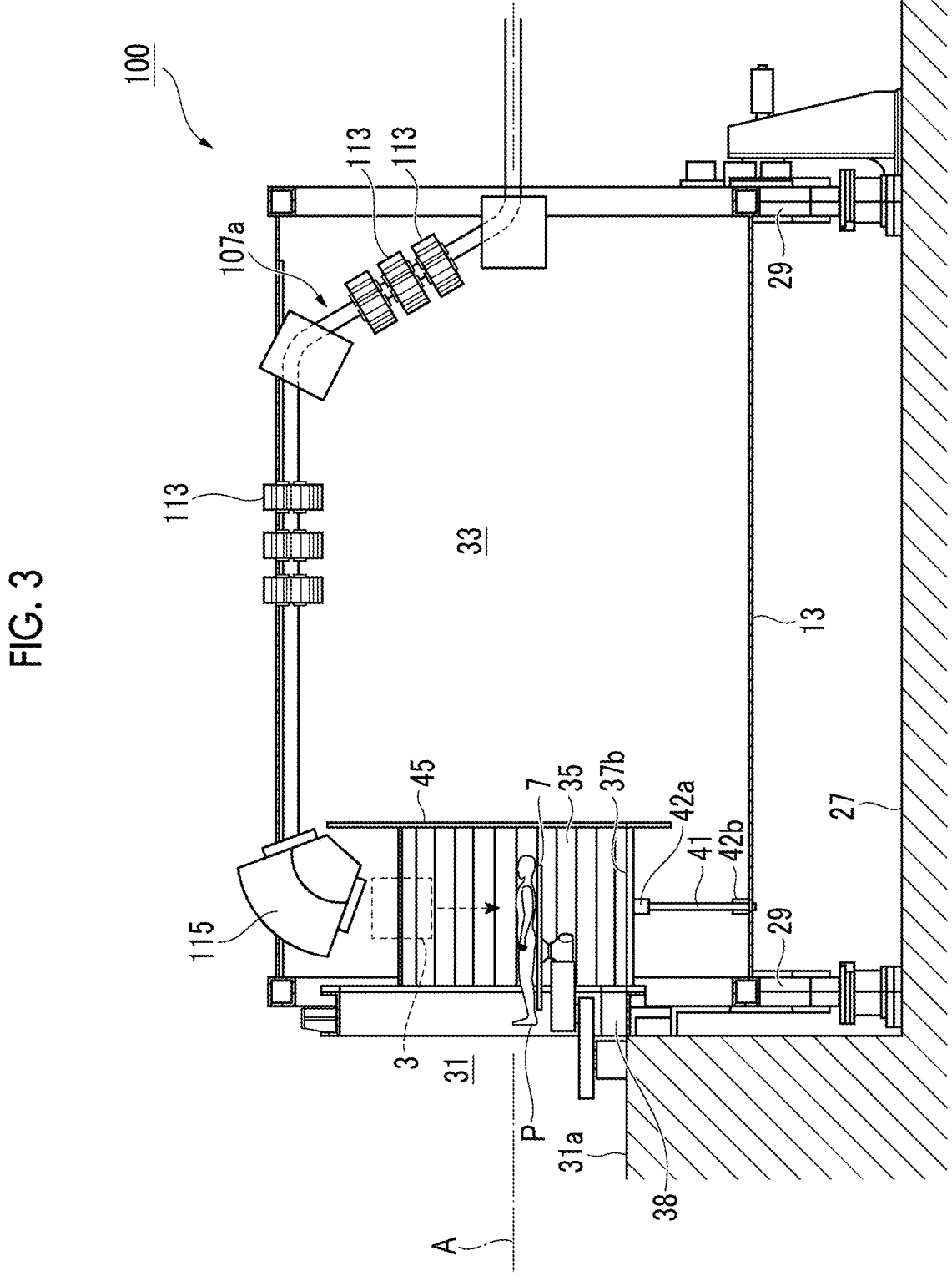
FIG. 3 is a sectional view of the charged particle beam irradiation apparatus, which is a vertical section including a rotation axis.

FIG. 2 is a perspective view showing a state where the charged particle beam irradiation apparatus 100 is viewed from a treatment room side. FIG. 3 is a sectional view of the charged particle beam irradiation apparatus 100, which is a vertical section including the rotation axis, and FIG. 4 is a sectional view of the charged particle beam irradiation apparatus 100, which is a vertical section perpendicular to the rotation axis.

Figure 4:
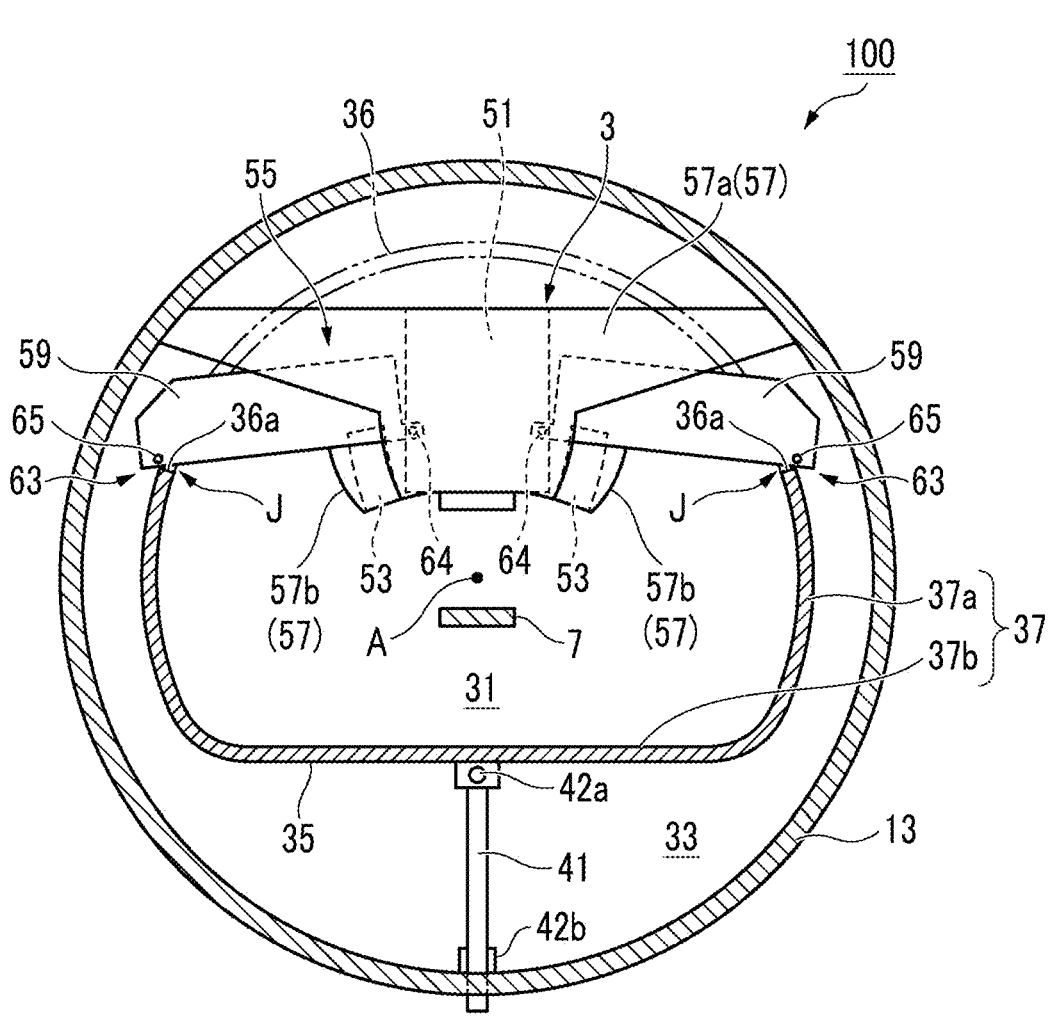
FIG. 4 is a sectional view of the charged particle beam irradiation apparatus, which is a vertical section perpendicular to the rotation axis.

As shown in FIGS. 2 to 4, the rotating gantry 13 has a cylindrical shape with the rotation axis A as a cylindrical axis. The length of the rotating gantry 13 in an axial direction is, for example, 8 m, and a diameter thereof is, for example, 6 m. The rotating gantry 13 is not limited to a rotatable cylindrical shape and may be configured to include a frame body that is oscillatable 180° about the rotation axis A. The irradiator 3 is disposed on a cylinder inner peripheral surface side of the rotating gantry 13, and the irradiator 3 is fixed to the rotating gantry 13 via a predetermined support frame. As the rotating gantry 13 rotates about the rotation axis A, the irradiator 3 moves rotationally about the rotation axis A in a posture in which an emission direction of a charged particle beam is directed to a radial inner side of the rotating gantry 13. That is, the irradiator 3 can rotationally move in the vicinity of the patient P disposed on the rotation axis A on the treatment table 7 and can irradiate the patient P with charged particle beams from various directions. The treatment table 7 is fixed to a structure 27 of a building via an arm for moving the treatment table 7 in the treatment room.

Since the rotating gantry 13 is rotated as described above, as shown in FIG. 3, roller devices 29 are provided at two places on a floor surface of the structure 27 below the rotating gantry 13. Outer peripheral surfaces of both end portions of the rotating gantry 13 in the axial direction are in contact with the roller devices 29 respectively, and as the roller devices 29 are driven by a motor (not shown), a rotational driving force about the rotation axis A is applied to the rotating gantry 13. In addition, the rotation of the rotating gantry 13 is stopped by brake devices (not shown) of the roller devices 29.

Figure 5:
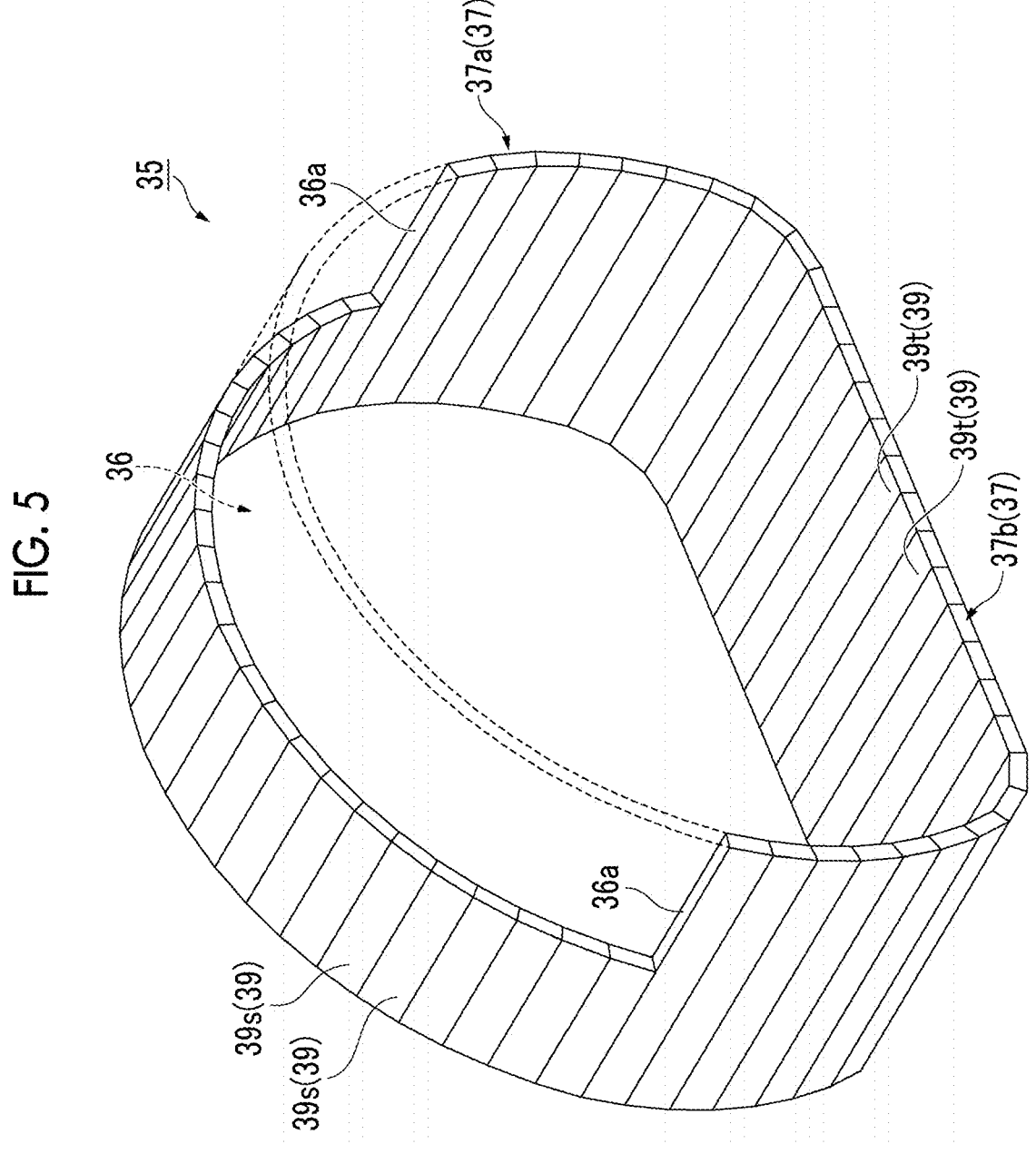
FIG. 5 is a perspective view showing a state where a moving floor of the charged particle beam irradiation apparatus is taken out and viewed from a machine room side.

A treatment room 31 where the treatment table 7 is disposed is disposed from the inside of the structure 27 to a part of an inner region of the rotating gantry 13. As shown in FIGS. 2 to 4, in order to partition the treatment room 31 from a machine room 33 on the inner side of the rotating gantry 13, a moving floor 35 is provided on the inner side of the rotating gantry 13. FIG. 5 is a perspective view showing a state where the moving floor 35 is taken out and viewed from a machine room 33 side. As shown in FIGS. 4 and 5, the moving floor 35 extends in an annular shape over the entire annular trajectory 37 that annularly surrounds the rotation axis A and spreads with a predetermined width (for example, a width of approximately 2 m) in a rotation axis A direction like a band. The moving floor 35 moves on the annular trajectory 37 as the rotating gantry 13 rotates. The annular trajectory 37 includes a curved portion 37a that extends along a rotation circumferential direction of the rotating gantry 13 and the irradiator 3 when viewed from a line of sight parallel to the rotation axis A (viewed as in FIG. 4) and a horizontal portion 37b that extends horizontally to connect two lower end portions of the curved portion 37a to each other and has a tunnel shape as a whole. An inner space of the annular trajectory 37 is a part of the treatment room 31, and the patient P, treatment staff, or the like who is involved in treatment can come into and go out of this space.

As shown in FIG. 3, the structure 27 is provided with a fixing ring 38 that cantilevers the moving floor 35 overhanging in the inner region of the rotating gantry 13 and that guides the movement of the moving floor 35. The fixing ring 38 is provided in a tunnel shape along the annular trajectory 37 when viewed from the line of sight parallel to the rotation axis A and holds the moving floor 35 in a state where the movement of the moving floor 35 on the annular trajectory 37 is allowed. As shown in FIG. 5, the moving floor 35 is configured by multiple floor members 39 arrayed and spread on the annular trajectory 37, and each of the floor members 39 is slidably held by the fixing ring 38. The floor member 39 is a long plate-shaped member extending in the rotation axis A direction. The floor members 39 adjacent to each other may be coupled to each other to be relatively rotatable about an axis parallel to the rotation axis A. With this structure, the moving floor 35 is bendable between the floor members 39 and is movable on the annular trajectory 37 while bending and deforming in accordance with the shape of the annular trajectory 37 as a whole.

The moving floor 35 has stiffness and strength which are enough to support the weight of a person, in a state of being cantilevered by the fixing ring 38. As shown in FIG. 3, there is the horizontal portion 37b of the annular trajectory 37 along a floor 31a of the treatment room 31 in the structure 27, and an upper surface of the moving floor 35 at the horizontal portion 37b is positioned substantially flush with the floor 31a. Therefore, the patient P, the treatment staff, or the like who is involved in treatment can walk on the floor 31a and the moving floor 35 extended from the floor 31a in the treatment room 31.

A mechanism for moving the moving floor 35 on the annular trajectory 37 is as follows. As shown in FIGS. 3 and 4, the moving floor 35 is connected to the rotating gantry 13 via a drive rod 41 that extends in a rotation radial direction. One end of the drive rod 41 is connected to one of the floor members 39 configuring the moving floor 35 via a hinge portion 42a having a hinge axis parallel to the rotation axis A. The other end of the drive rod 41 is slidably held in the rotation radial direction by a rod holding unit 42b of the rotating gantry 13. The rod holding unit 42b has, for example, a structure of an LM guide.

With this mechanism, when the roller devices 29 rotate the rotating gantry 13 about the rotation axis A, a driving force in the rotation circumferential direction is transmitted also to the moving floor 35 via the drive rod 41, and the moving floor 35 moves on the annular trajectory 37 to follow the rotating gantry 13. In this case, when a distance between the hinge portion 42a and the rod holding unit 42b changes due to the movement of the moving floor 35, the distance change is absorbed as the other end side of the drive rod 41 slides with the rod holding unit 42b in a radial direction. In this case, the drive rod 41 slidably penetrates the rotating gantry 13 in the radial direction, and thereby the rotating gantry 13 is provided with a space for inserting the sliding drive rod 41.

In addition to the moving floor 35 described above, a vertical partition wall 45 that partitions the inner side of the rotating gantry 13 into the treatment room 31 and the machine room 33 in the rotation axis A direction is provided. The vertical partition wall 45 is disposed along an edge of the moving floor 35 on a back side when viewed from the inside of the treatment room 31 in a vertical posture perpendicular to the rotation axis A. For example, the vertical partition wall 45 has a disk shape that has a diameter slightly smaller than the inner diameter of the rotating gantry 13 and that has a center at the position of the rotation axis A. For example, a motor (not shown) that rotates the vertical partition wall 45 is fixed to the rotating gantry 13, and the vertical partition wall 45 is made rotatable about the rotation axis A relative to the rotating gantry 13 by the motor. When the roller devices 29 rotate the rotating gantry 13, to cancel out this rotation, the motor reversely rotates the vertical partition wall 45, and the vertical partition wall 45 is brought into a stationary state with respect to the treatment room 31. Therefore, the vertical partition wall 45 functions as a stationary vertical wall for partitioning into the treatment room 31 and the machine room 33.

In addition, as shown in FIGS. 1 and 3, a part of the transportation line 107 on a downstream side (referred to as a "transportation line 107a") is supported by the rotating gantry 13. The transportation line 107a includes, for example, the quadrupole electromagnet 113 that converges charged particle beams, the bending magnet 115 that bends the charged particle beams, and the like. A downstream end of the transportation line 107a is connected to the irradiator 3, and an upstream end of the transportation line 107a is connected to a rotation mechanism (not shown) with respect to a portion of the transportation line 107 on the upstream side. The transportation line 107a rotates about the rotation axis A as the rotating gantry 13 rotates.

As shown in FIGS. 2 to 4, the irradiator 3 protrudes into the treatment room 31 from the machine room 33 side across the annular trajectory 37. The irradiator 3 includes an irradiation nozzle 51 that irradiates the patient P on the treatment table 7 with charged particle beams transmitted from the transportation line 107a. Further, the irradiator 3 includes a pair of X-ray pipes 53 provided such that the irradiation nozzle 51 is sandwiched therebetween in the rotation circumferential direction and the support frame (not shown) that fixes the irradiation nozzle 51 and the X-ray pipes 53 to the rotating gantry 13. The X-ray pipes 53 are a part of a CT device (not shown), and the CT device is used in CT imaging of the patient P. The position of a lesion or the like of the patient P is recognized through a CT image obtained by CT imaging, and the patient P is positioned on the treatment table 7.

In order to make the irradiator 3 protrude into the treatment room 31, as shown in FIG. 5, the moving floor 35 is provided with an irradiator insertion port 36. The multiple floor members 39 configuring the moving floor 35 include two types including a type having a large length in the rotation axis A direction (referred to as a "floor member 39t") and a type having a small length (referred to as a "floor member 39s"). The moving floor 35 has two regions including a region where the floor members 39t are consecutively disposed and a region where the floor members 39s are consecutively disposed. Among the regions, in the region where the floor members 39s are consecutively disposed, there are the floor members 39s on a front side when viewed from the inside of the treatment room 31, and a state where the above irradiator insertion port 36 is formed between the vertical partition wall 45 (FIG. 3) on the back side and the floor members 39s is caused. The irradiator 3 is inserted into the irradiator insertion port 36 and protrudes into the treatment room 31.

Figure 6:
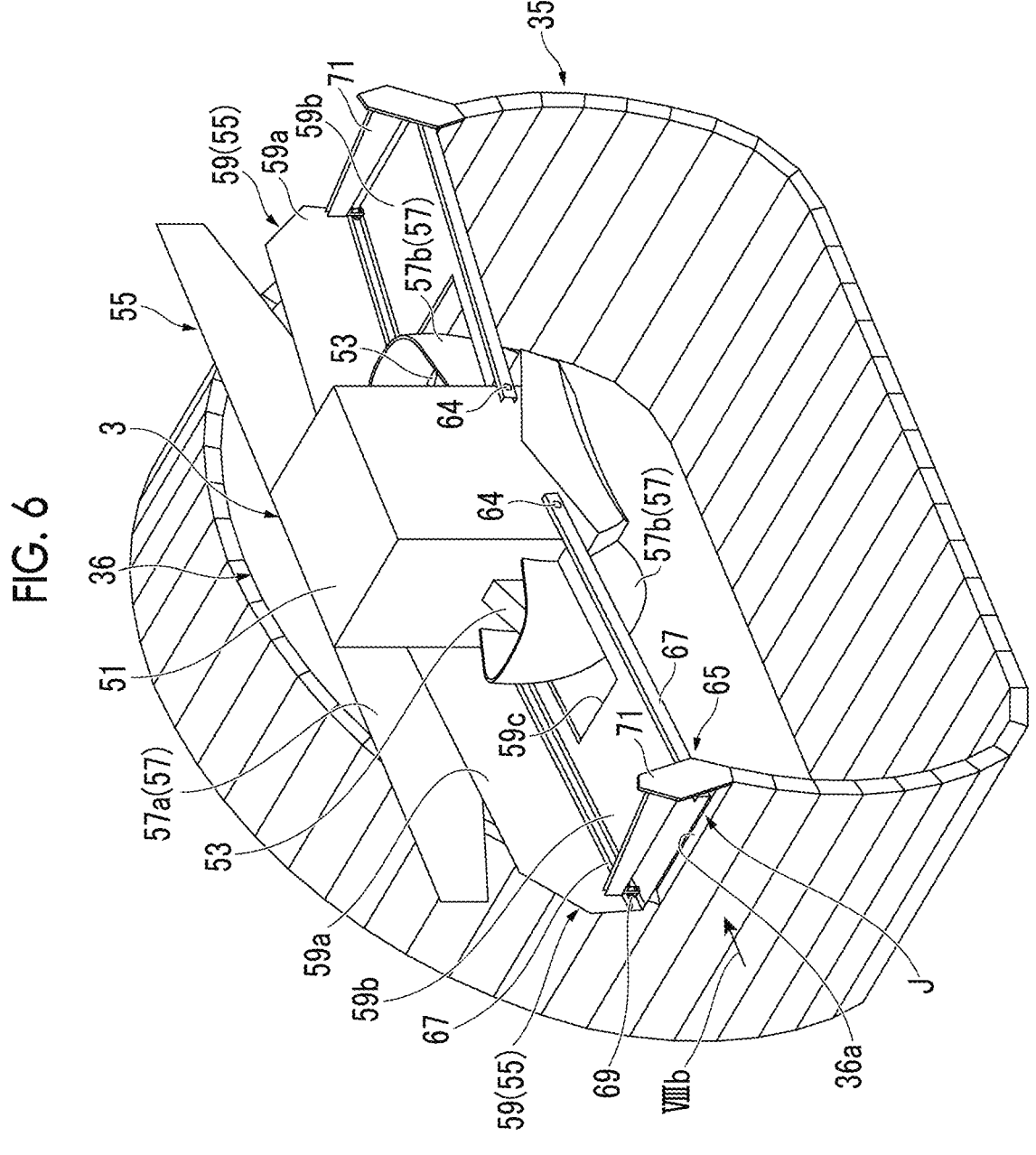
FIG. 6 is a perspective view showing a state where a positional relationship between the moving floor of FIG. 5 and an irradiator is viewed from the machine room side.
Figure 7:
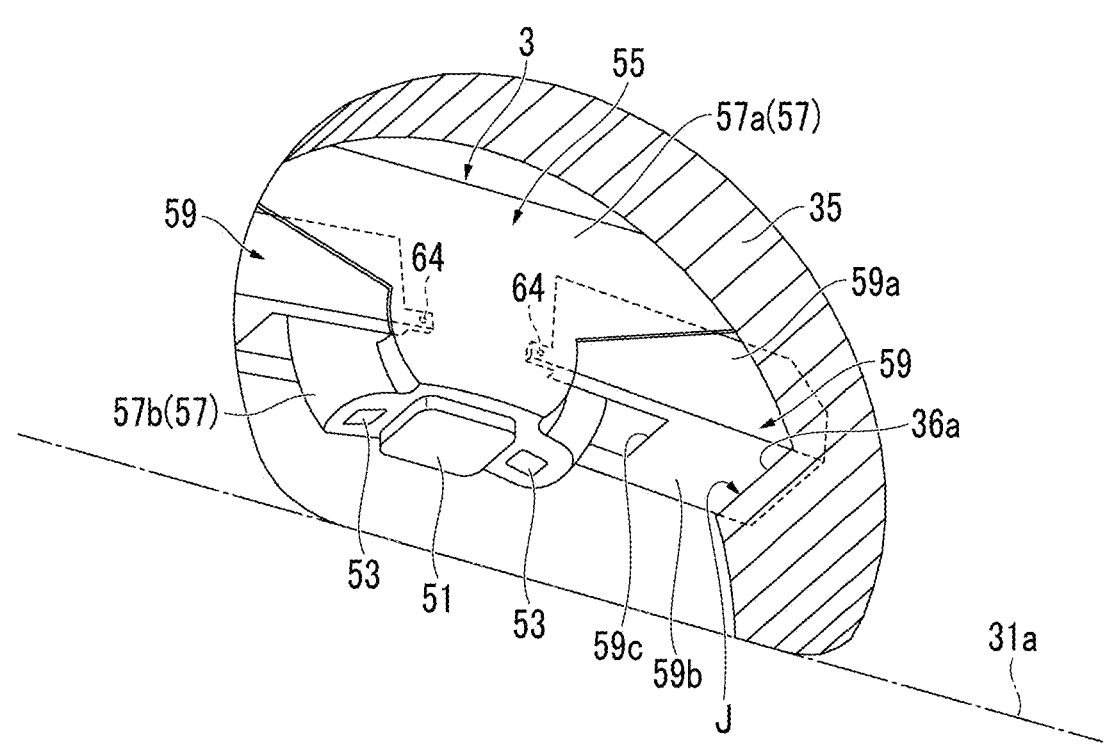
FIG. 7 is a perspective view showing a state where surroundings of the irradiator protruding to the treatment room side are looked up from the treatment room side.

FIG. 6 is a perspective view showing a state where a positional relationship between the moving floor 35 of FIG. 5 and the irradiator 3 inserted into the irradiator insertion port 36 is viewed from the machine room 33 side. FIG. 7 is a perspective view showing a state where surroundings of the irradiator 3 protruding to a treatment room 31 side are looked up from the treatment room 31 side. As shown in FIGS. 4, 6, and 7, the irradiator 3 protrudes from the irradiator insertion port 36 into the treatment room 31, and the irradiator 3 is provided with an irradiator cover 55 for covering the irradiation nozzle 51 and the X-ray pipes 53. As shown in FIG. 7, main portions of the irradiation nozzle 51 and the X-ray pipes 53 cannot be viewed from the treatment room 31 side as being covered with the irradiator cover 55.

The irradiator cover 55 includes a fixed cover 57 of which a position is fixed to the irradiation nozzle 51 and the X-ray pipes 53 and a movable cover 59 that is displaceable with respect to the irradiation nozzle 51 and the X-ray pipes 53. The fixed cover 57 includes an irradiation nozzle cover 57a that covers a front surface side and a lower surface side of the irradiation nozzle 51 when viewed from the inside of the treatment room 31 and an X-ray pipe cover 57b that covers the vicinity of the X-ray pipes 53 and that has a bent shape. The irradiation nozzle cover 57a and the X-ray pipe cover 57b are connected to each other below the movable cover 59. The fixed cover 57 may be fixed, for example, to the above support frame (not shown) that fixes the irradiation nozzle 51 and the X-ray pipes 53 to the rotating gantry 13. Above the irradiation nozzle cover 57a, a gap is generated between the curved portion 37a of the annular trajectory 37 and the irradiation nozzle cover 57a, but the gap is closed, for example, by an end surface of the support frame.

The movable cover 59 is positioned adjacent to an edge portion 36a (FIGS. 4 and 5) of the irradiator insertion port

Figure 8A:
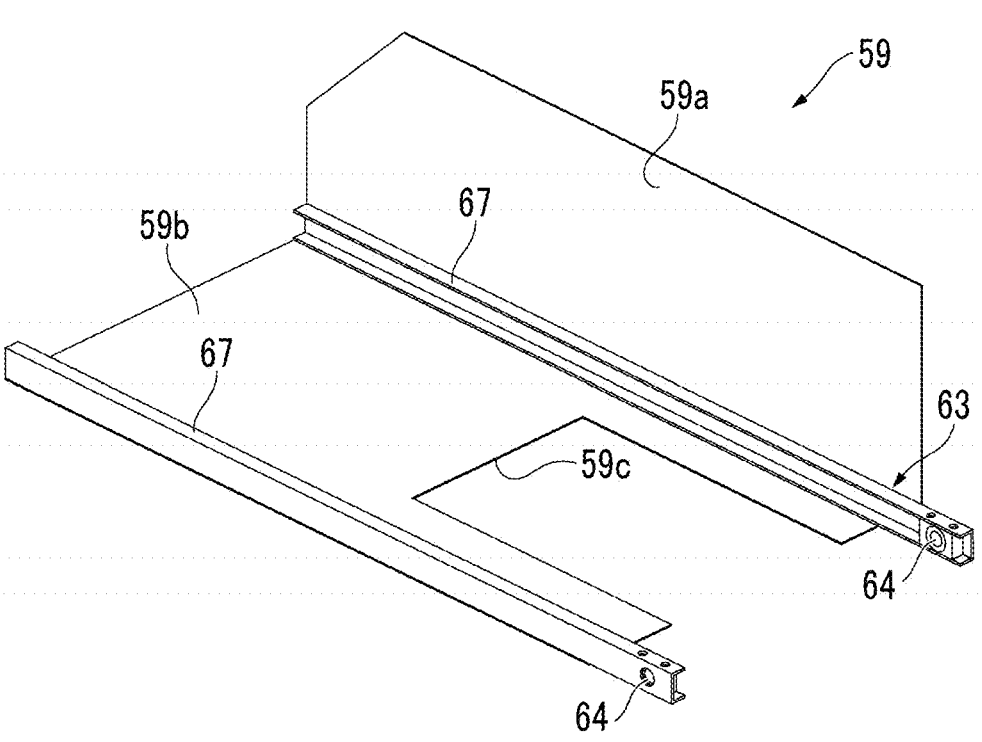
FIG. 8A is a perspective view showing a movable cover.

36 of the moving floor 35 in a moving direction. In addition, one end of the movable cover 59 is supported by the irradiator 3. Between the movable cover 59 and the edge portion 36*a*, a gap J is formed in the moving direction of the moving floor 35. Specifically, a parallel cover portion 59*b* of the movable cover 59 to be described later faces the edge portion 36*a* of the moving floor 35 with the gap J placed. As shown in FIG. 4, since there are the edge portions 36*a* at both of the front and the rear of a rotation direction when viewed from the irradiator 3, in response to this, a pair of movable covers 59 are provided symmetrically at the front and the rear with the irradiator 3 sandwiched therebetween. FIG. 8A is a perspective view showing the movable cover 59. Although FIG. 8A shows one of the pair of movable covers 59, the other movable cover 59 has a shape bilaterally symmetrical to FIG. 8A, and thereby showing and description thereof will be omitted.

As shown in FIG. 8A, the movable cover 59 has an L-shaped section as a whole and includes a perpendicular cover portion 59*a* that is positioned in a plane perpendicular to the rotation axis A and the parallel cover portion 59*b* that is positioned in a plane parallel to the rotation axis A. A rectangular cutout 59*c* for avoiding interference with the X-ray pipe cover 57*b* of the fixed cover 57 is formed in the parallel cover portion 59*b*. One end of the movable cover 59 is supported by the irradiation nozzle 51 at a hinge portion 64, and the hinge portion 64 has a hinge axis parallel to the rotation axis A. That is, when viewed from the line of sight parallel to the rotation axis A (when viewed as in FIG. 4), the movable cover 59 is supported by the irradiation nozzle 51 on one end side to be pivotable about the hinge portion 64. As shown in FIG. 4, on the irradiation nozzle 51, the hinge portion 64 is provided at a place positioned in an inner region of the annular trajectory 37 at all times regardless of a rotation position of the irradiator 3. The other end of the movable cover 59 reaches an outer position of the annular trajectory 37, and a part on the other end side overhangs to the outer side of the annular trajectory 37.

The rotating gantry 13 is provided with an adjusting mechanism 63 that can adjust a pivoting position of the movable cover 59 to correspond to the rotational movement of the irradiator 3 such that the gap J is covered at all times regardless of the rotation position of the irradiator 3. The expression "the gap J is covered" does not necessarily mean a state where the gap J is zero and means a state where the gap J is sufficiently small such that a part or all of the body of a person (for example, the patient P, treatment staff, apparatus maintenance staff, or the like) in the treatment room 31 does not enter the gap J. In addition, the size of the gap J adjusted by the adjusting mechanism 63 maybe further smaller than the above. For example, the size of the gap J adjusted by the adjusting mechanism 63 may satisfy a condition in which the machine room 33 cannot be viewed through the gap J from the inside of the treatment room 31 at all times regardless of the rotation position of the irradiator 3. The adjusting mechanism 63 includes the above hinge portion 64 (first support portion) that is provided at the irradiation nozzle 51 of the irradiator 3 and that supports one end portion of the movable cover 59 and an outer end side support portion 65 (second support portion) that is provided at the moving floor 35 and that supports the other part of the movable cover 59.

The outer end side support portion 65 has a mechanism that allows displacement of the movable cover 59 in a linear direction connecting the outer end side support portion 65 and the hinge portion 64 to each other. The outer end side support portion 65 also allows the rotation of the movable cover 59 about the outer end side support portion 65. As a specific example of such a mechanism, the adjusting mechanism 63 includes a guide rail 67 (FIG. 8A) that is provided at the movable cover 59 and that has a U-shaped section. The guide rail 67 extends on a line connecting the hinge portion 64 and the outer end side support portion 65 to each other. The two guide rails 67 are provided at both edges of the parallel cover portion 59*b* respectively and extend parallel to a direction perpendicular to the rotation axis A. The hinge portion 64 is positioned at one end portion of the guide rail 67. The outer end side support portion 65 includes a roller 69 (FIG. 8B) that engages with the guide rail 67 and that rolls on the guide rail 67.

Figure 8B:
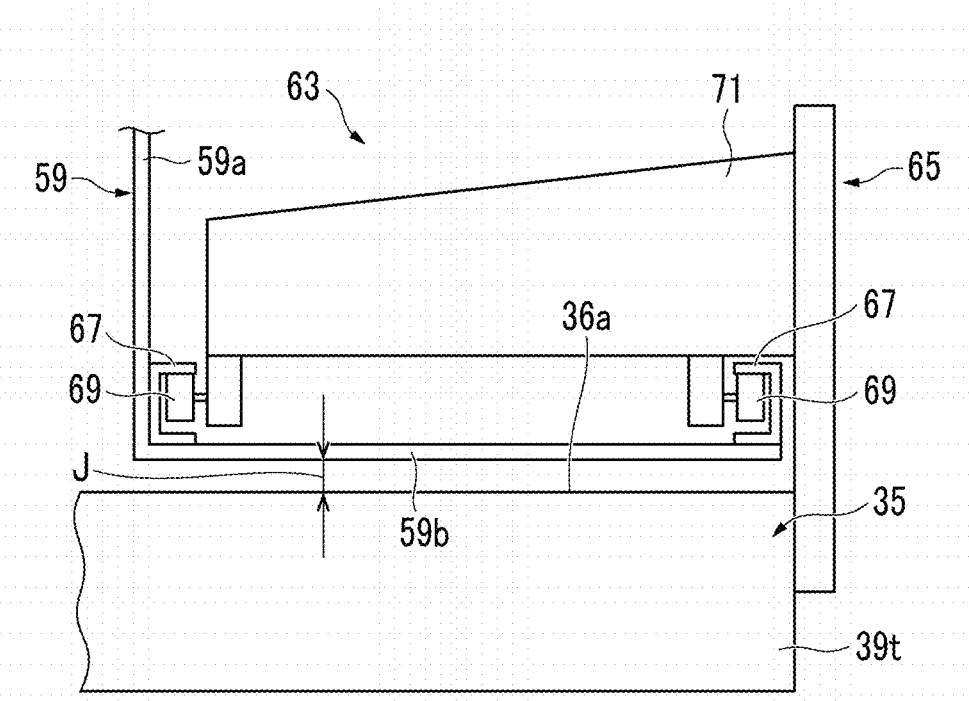
FIG. 8B is an arrow view including a roller viewed from an arrow VIIIb direction in FIG. 6.

FIG. 8B is an arrow view including the roller 69 viewed from an arrow VIIIb direction in FIG. 6. As shown in FIG. 8B, the outer end side support portion 65 includes a bracket 71 fixed to the floor member 39*t* forming the edge portion 36*a* of the moving floor 35. The bracket 71 extends in the rotation axis A direction at a position where the parallel cover portion 59*b* is sandwiched between the edge portion 36*a* and the bracket 71. The outer end side support portion 65 includes the rollers 69 provided at both ends of the bracket 71 in the rotation axis A direction, respectively. In the present embodiment, when viewed from the line of sight parallel to the rotation axis A as shown in FIG. 4, the two rollers 69 are positioned slightly on the outer side of the annular trajectory 37 and are positioned in the immediate vicinity of the edge portion 36*a* of the irradiator insertion port 36. As each roller 69 is fitted into each inner side of the guide rail 67 and rolls in the guide rail 67, the movable cover 59 can be displaced in an extending direction of the guide rail 67 with respect to the roller 69.

Operational effects caused by the charged particle beam irradiation apparatus 100 including the rotating gantry 13 and the irradiator 3 which are described above will be described. As described above, the irradiator 3 rotates on a circular trajectory as the rotating gantry 13 rotates. On the other hand, the moving floor 35 moves on the non-circular annular trajectory 37 as the rotating gantry 13 rotates. As described above, since movement trajectories of the irradiator 3 and the rotating gantry 13 do not match each other, when the movable cover 59 is fixed to the irradiator 3, the size of the gap J changes as the irradiator 3 and the moving floor 35 rotate, as geometrically understood. In particular, since the irradiator 3 is configured to protrude into the treatment room 31 across the annular trajectory 37 of the moving floor 35 in the present embodiment, changes in the size of the gap J are remarkable.

Figure 9:
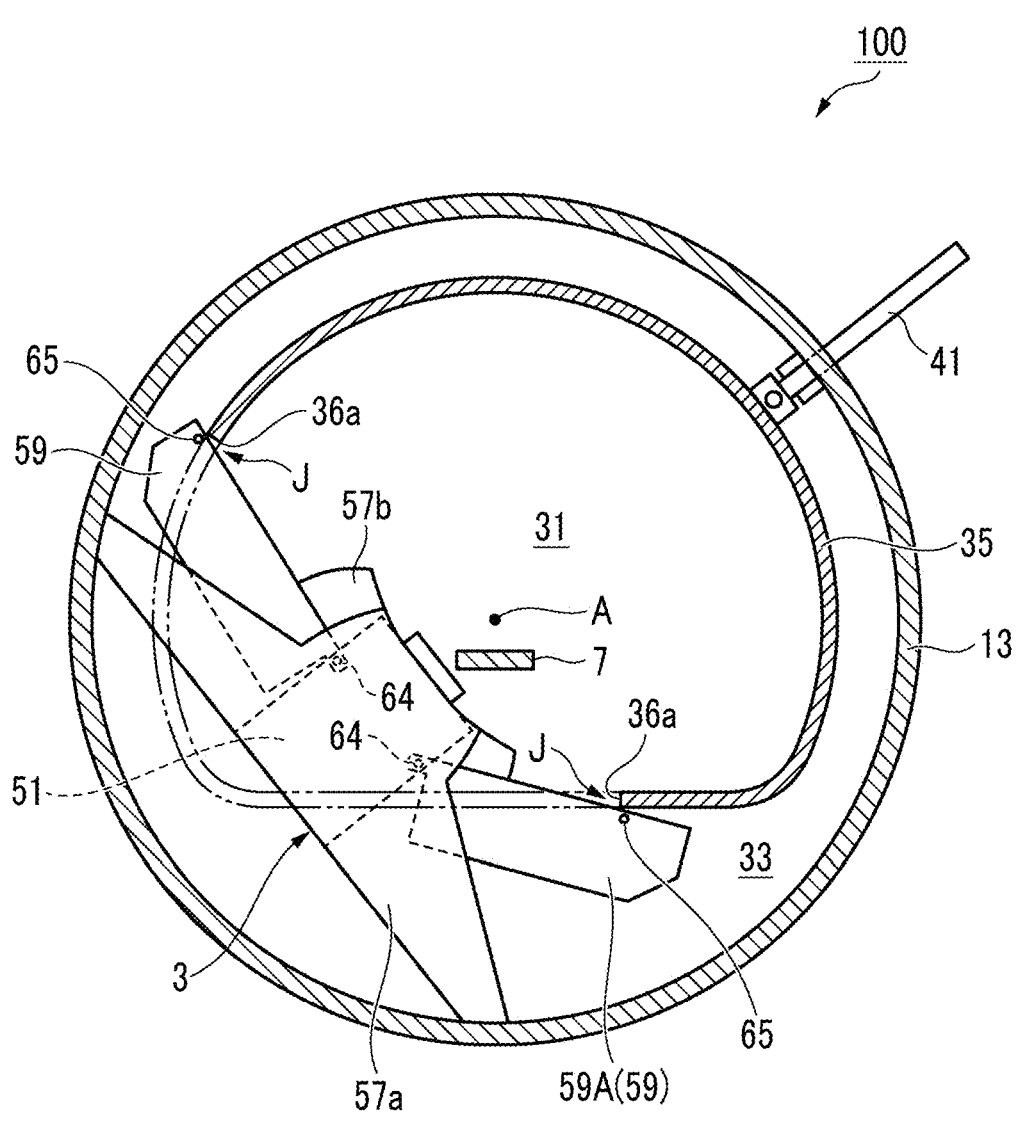
FIG. 9 is a sectional view showing a state where the irradiator has rotationally moved obliquely below a treatment table from the state of FIG. 4.

Meanwhile, in the charged particle beam irradiation apparatus 100, the movable cover 59 is supported pivotably with respect to the irradiator 3, the pivoting position of the movable cover 59 is adjusted by the adjusting mechanism 63 depending on the rotation position of the irradiator 3, and the gap J is covered at all times. For example, as shown in FIG. 9, when the irradiator 3 has moved obliquely below the treatment table 7, compared to the state of FIG. 4, one (shown by a reference sign 59A in FIG. 9) of the movable covers 59 changes the pivoting position relatively counterclockwise with respect to the irradiator 3 and is displaced to considerably overhang to the outer side of the annular trajectory 37 (that is, is displaced to considerably enter the machine room 33 side). As described above, as the movable cover 59 changes the pivoting position, the gap J is covered.

In addition, since the movable cover 59 is configured such that the pivoting position is changed with respect to the irradiator 3 to cover the gap J, it is not necessary to deform the movable cover 59 itself in accordance with the size of the gap J. Therefore, the movable cover 59 can be configured by a hard non-flexible member, and for example, it is possible to give stiffness and strength, which are enough to support the weight of a person, to the movable cover 59. For example, unlike the retractable cover of the related art described above, the movable cover 59 may be made of a metal. Then, for example, in a case where the movable cover 59A is positioned in the surroundings of the horizontal portion 37b of the annular trajectory 37 as shown in FIG. 9, even when the patient P, treatment staff, or the like on the moving floor 35 has stepped on the movable cover 59A, the movable cover 59A can safely support the weight of the patient P, the treatment staff, or the like. That is, since the patient P, the treatment staff, or the like can safely walk on the moving floor 35, a gap between the irradiator 3 and the moving floor 35 is covered with the movable cover 59A, and it can be said that it is in a state where safety can be ensured.

In addition, in a case where the size of the gap J adjusted by the adjusting mechanism 63 satisfies a condition in which the machine room 33 cannot be viewed from the inside of the treatment room 31 through the gap J at all times regardless of the rotation position of the irradiator 3, a mechanical structure of the machine room 33 can be hidden from the patient P involved in treatment and cannot be viewed through the gap J.

In addition, when a method in which the gap J is covered with the retractable cover is adopted, since it is necessary to apply tension to the retractable cover, there is a possibility in which the retractable cover is likely to be damaged and maintenance frequency increases. On the contrary, since it is not necessary to apply tension to the movable cover 59, the life of the cover is extended compared to the method in which the retractable cover is used.

In addition, in the adjusting mechanism 63, one end portion of the movable cover 59 is supported by the irradiation nozzle 51 via the hinge portion 64, the other part of the movable cover 59 is supported by the outer end side support portion 65 in the immediate vicinity of the edge portion 36a, and the outer end side support portion 65 forms a mechanism that allows the displacement of the movable cover 59 in the linear direction connecting the outer end side support portion 65 and the hinge portion 64 to each other. Since the movable cover 59 automatically changes the pivoting position and passes through the outer end side support portion 65 in the immediate vicinity of the edge portion 36a at all times with such a mechanism, the gap J is automatically covered with the movable cover 59.

As a result, a state where the gap J between the parallel cover portion 59b and the edge portion 36a is covered is maintained at all times regardless of the rotation position of the irradiator 3. As described above, since the movable cover 59 automatically pivots, a power source for driving the movable cover 59 or a control unit for controlling a pivot angle of the movable cover 59 is unnecessary. In addition, since the adjusting mechanism 63 is configured by simple mechanical elements including the hinge portion 64 that supports the movable cover 59, the guide rail 67 that is provided at the movable cover 59 and that has a U-shaped section, and the roller 69 that rolls on the guide rail 67, the adjusting mechanism 63 can be configured by general-purpose components.

In addition, the moving floor 35 is configured by the floor members 39t and 39s arrayed in the moving direction. Among the floor members 39t and 39s, in the region where the floor members 39s are consecutively disposed, there are the floor members 39s of the moving floor 35 only on the front side when viewed from the inside of the treatment room 31, and there is the irradiator 3 protruding from the irradiator insertion port 36 to the back side. Therefore, in a case where the irradiator 3 is positioned at the horizontal portion 37b of the annular trajectory 37, the patient P, the treatment staff, or the like in the treatment room 31 can walk on the moving floor 35 by stepping on the floor members 39s on the front side of the irradiator 3.

In addition, since the movable cover 59 is supported by the hinge portion 64 positioned in the inner region of the annular trajectory 37 and can protrude to an outer region of the annular trajectory 37 (to the machine room 33 side) across the annular trajectory 37, also in a case where a distance between the hinge portion 64 and the roller 69 is the largest, the protrusion portion enters the inner region of the annular trajectory 37, and the gap J can be covered with the movable cover 59.

In addition, the moving floor 35 has the floor members 39 arrayed and spread on the annular trajectory 37 in the moving direction of the moving floor 35 and is bendable between the floor members 39. With this configuration, as the moving floor 35 is deformable in accordance with the tunnel shape of the annular trajectory 37, and the moving floor 35 is formed by the multiple floor members 39 in which the annular trajectory 37 is embedded without excess or deficiency, the walking safety of the patient P, the treatment staff, or the like on the moving floor 35 can be ensured.

The present invention can be performed in a variety of forms with various changes and improvements based on the knowledge of those who are skilled in the art, including the embodiments described above. In addition, it is also possible to configure a modification example by using technical matters described in the embodiments described above. The configurations of the respective embodiments or the like may be combined and used as appropriate.

Figure 10:
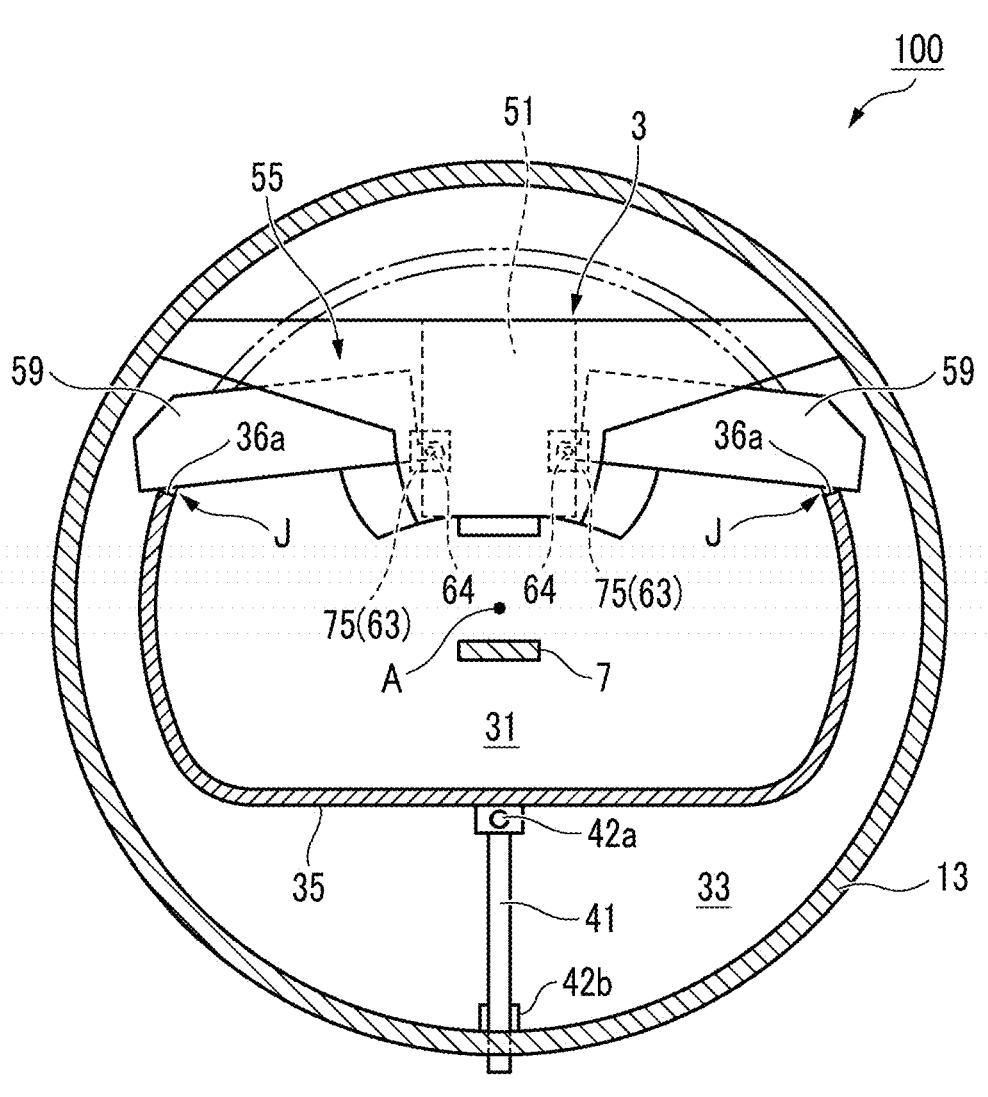
FIG. 10 is a sectional view of the charged particle beam irradiation apparatus including a modification example of an adjusting mechanism.

For example, although the adjusting mechanism 63 pivots the movable cover 59 without including a power source in the embodiments described above, the adjusting mechanism 63 may have a power source for pivoting the movable cover 59. As an example of this, as shown in FIG. 10, the adjusting mechanism 63 may have a stepping motor 75 that pivots the movable cover 59 about the hinge portion 64 with respect to the irradiation nozzle 51 and a control circuit (not shown) that controls a rotation angle of the stepping motor 75. The control circuit controls the rotation angle of the stepping motor 75 to adjust the pivoting position of the movable cover 59 such that the parallel cover portion 59b of the movable cover 59 is positioned in the immediate vicinity of the edge portion 36a of the moving floor 35 (FIG. 5) at all times. That is, the pivoting position of the movable cover 59 is adjusted through the control of the stepping motor 75 by the control circuit, and a state where the gap J is covered at all times is caused. In this case, it is also possible to omit the outer end side support portion 65 including the guide rail 67 and the roller 69. Since the movable cover 59 does not allow a force to act on the moving floor 35 when the outer end side support portion 65 including the guide rail 67 and the roller 69 is omitted and the stepping motor 75 and the control circuit are adopted, the operation stability of the moving floor 35 increases. In addition, when the stepping motor 75 and the control circuit are adopted in addition to the outer end side support portion 65 including the guide rail 67 and the roller 69, the operation stability of the movable cover 59 and the moving floor 35 increases.

In addition, although a mechanism in which the guide rail 67 and the roller 69 are combined is adopted in the outer end side support portion 65 in the embodiments described above as a mechanism that allows the displacement of the movable cover 59 in the linear direction connecting the outer end side support portion 65 and the hinge portion 64 to each other, the outer end side support portion 65 is not limited to this mechanism. For example, the outer end side support portion 65 may adopt a mechanism that slidably connects the movable cover 59 and the moving floor 35 to each other via the LM guide.

In addition, although the movable cover 59 is supported pivotally with respect to the irradiator 3 in the embodiments described above, an object, by which the movable cover 59 is pivotally supported, is not limited to the irradiator 3. For example, the movable cover 59 is pivotally supported with respect to the moving floor 35 such that a gap between the movable cover 59 and the moving floor 35 is covered, and the adjusting mechanism 63 may include a power source (for example, a motor) for pivoting the movable cover 59.

In addition, the size of the gap J may change depending on the position of the irradiator 3. However, in this case, the size of the gap J changes within a range that is sufficiently small such a part or all of the body of a person in the treatment room 31 does not enter the gap. Alternatively, the size of the gap J changes within a range that satisfies a condition in which the machine room 33 cannot be viewed through the gap J from the inside of the treatment room 31 at all times regardless of the rotation position of the irradiator 3.

It should be understood that the invention is not limited to the above-described embodiment, but may be modified into various forms on the basis of the spirit of the invention. Additionally, the modifications are included in the scope of the invention.

What is claimed is:

1. A particle beam treatment apparatus comprising:
an irradiator that has an irradiation nozzle which irradiates an irradiation target with a particle beam and that is capable of moving rotationally in a vicinity of the irradiation target;
a moving floor that extends on an annular trajectory surrounding the irradiation target along a rotation circumferential direction of the irradiator and that is movable on the annular trajectory depending on a position of the irradiator;
a movable cover that is supported pivotally with respect to the irradiator or the moving floor and that covers a gap between the irradiator and the moving floor; and
an adjustor that includes a guide rail and that is configured to adjust a pivoting position of the movable cover depending on the position of the irradiator such that a gap between the movable cover and the moving floor is covered,
wherein the movable cover includes
a perpendicular cover portion that is positioned in a plane perpendicular to a rotation axis of the irradiator and that covers the gap between the irradiator and the moving floor when viewed from a direction of the rotation axis, and
a parallel cover portion that is positioned in a plane parallel to the rotation axis of the irradiator.

2. The particle beam treatment apparatus according to claim 1, further comprising:
a transportation line; and
a rotating gantry,
wherein a downstream end of the transportation line is connected to the irradiator, and
a part of the transportation line on a downstream side is supported by the rotating gantry.

3. The particle beam treatment apparatus according to claim 2,
wherein the irradiation nozzle is disposed on a cylinder inner peripheral surface side of the rotating gantry, and
the irradiator includes a pair of X-ray pipes that are provided such that the irradiation nozzle is sandwiched therebetween in the rotation circumferential direction.

4. The particle beam treatment apparatus according to claim 3,
wherein the irradiator further includes a support frame that fixes the irradiation nozzle and the X-ray pipes to the rotating gantry and is fixed to the rotating gantry via the support frame.

5. The particle beam treatment apparatus according to claim 4,
wherein the irradiator moves rotationally about the rotation axis in a posture in which an emission direction of a charged particle beam is directed to an inner side of the rotating gantry in a radial direction.

6. The particle beam treatment apparatus according to claim 5,
wherein the rotating gantry has a cylindrical shape with the rotation axis as a cylindrical axis.

7. The particle beam treatment apparatus according to claim 5,
wherein the rotating gantry includes a frame body that is oscillatable about the rotation axis.

8. The particle beam treatment apparatus according to claim 2,
wherein the transportation line includes a plurality of quadrupole electromagnets and a plurality of bending magnets.

9. The particle beam treatment apparatus according to claim 1,
wherein the movable cover is supported pivotally with respect to the irradiator,
the adjustor further includes
a first support portion that is provided at the irradiator and that supports one part of the movable cover, and
a second support portion that is provided at the moving floor and that supports the other part of the movable cover, and
the second support portion allows displacement of the movable cover in a linear direction connecting the second support portion and the first support portion to each other.

10. The particle beam treatment apparatus according to claim 9,
wherein the guide rail is provided at the movable cover and extends on a line connecting the first support portion and the second support portion to each other, and
the second support portion includes a roller that rolls on the guide rail.

11. The particle beam treatment apparatus according to claim 10,
wherein the roller is fitted into an inner side of the guide rail and rolls in the guide rail.

12. The particle beam treatment apparatus according to claim 1,
wherein the movable cover is supported pivotally with respect to the irradiator and is capable of protruding to an outer region of the annular trajectory across the annular trajectory.

13

13. The particle beam treatment apparatus according to claim 1, wherein the moving floor includes a plurality of floor members arrayed on the annular trajectory in a moving direction of the moving floor and is bendable between the floor members.

14. The particle beam treatment apparatus according to claim 1, wherein the annular trajectory includes a curved portion that extends in the rotation circumferential direction of the irradiator and a horizontal portion that is connected to the curved portion.

15. The particle beam treatment apparatus according to claim 13, wherein the plurality of floor members has two types including a first floor member having a large length in the direction of the rotation axis and a second floor member having a small length in the direction of the rotation axis,

the moving floor has two regions including a region where the first floor members are consecutively disposed and a region where the second floor members are consecutively disposed, and an irradiator insertion port for allowing the irradiator to protrude into a treatment room is formed in the region where the second floor members are consecutively disposed.

16. The particle beam treatment apparatus according to claim 1, wherein the irradiator includes an X-ray pipe, the particle beam treatment apparatus further comprises a fixed cover of which a position is fixed with respect to the irradiation nozzle and the X-ray pipe, and that includes an irradiation nozzle cover which covers a front surface side and a lower surface side of the irradiation nozzle and an X-ray pipe cover which covers a vicinity of the X-ray pipe, and the parallel cover portion is provided with a cutout for avoiding interference with the X-ray pipe.

* * * * *